(12) United States Patent
DeHaan (10) Patent No.: US 9,104,391 B2
(45) Date of Patent: *Aug. 11, 2015

(54) ADAPTIVELY OPTIMIZING ORDER ENTRY SYSTEM

(71) Applicant: Jan DeHaan, Hawley, PA (US)

(72) Inventor: Jan DeHaan, Hawley, PA (US)

(73) Assignee: CERNER INNOVATION, INC., Kansas City, KS (US)

( * ) Notice: Subject to any disclaimer, the term of this patent is extended or adjusted under 35 U.S.C. 154(b) by 45 days.

This patent is subject to a terminal disclaimer.

(21) Appl. No.: 13/860,739

(22) Filed: Apr. 11, 2013

(65) Prior Publication Data

US 2013/0218910 A1 Aug. 22, 2013

Related U.S. Application Data

(62) Division of application No. 12/268,776, filed on Nov. 11, 2008, now Pat. No. 8,447,778.

(60) Provisional application No. 60/988,120, filed on Nov. 15, 2007.

(51) Int. Cl.
*G06F 17/30* (2006.01)
*G06F 7/24* (2006.01)
(Continued)

(52) U.S. Cl.
CPC ............... *G06F 7/24* (2013.01); *G06F 19/325* (2013.01); *G06Q 10/10* (2013.01); *G06Q 50/22* (2013.01)

(58) Field of Classification Search
CPC .......................... G06F 17/30893; G06F 19/322
USPC .................................. 707/776, 807, 945, 796
See application file for complete search history.

(56) References Cited

U.S. PATENT DOCUMENTS 5,737,539 A 4/1998 Edelson et al.
5,754,939 A 5/1998 Herz et al.
(Continued)

FOREIGN PATENT DOCUMENTS

JP 2000 123098 4/2000

OTHER PUBLICATIONS

Franklin, "Modifiable Templates Facilitate Customization of Physician Order Entry", 1998, Proc AMIA Symp. 315-9.
(Continued)

*Primary Examiner* — Robert Beausoliel, Jr.
*Assistant Examiner* — Alexandria Bromell
(74) *Attorney, Agent, or Firm* — Shook, Hardy & Bacon L.L.P.

(57) ABSTRACT

A system continuously improves the sensitivity, specificity, precision, and accuracy of treatment ordering templates. A repository of information comprises multiple candidate order sets individually including multiple candidate items for order and associated corresponding related order parameters. An individual item for order is associated with multiple related order parameters. A data entry monitor monitors user selection of candidate items from a candidate order set and records candidate item usage data identifying items selected by a user for order from individual particular candidate order sets for multiple different candidate order sets. A data processor determines from the candidate item usage data at least one of, (a) data indicative of the number or proportion of candidate items of a particular candidate order set that were selected by a user during order entry and (b) data indicative of the number or proportion of candidate items of a particular candidate order set that were not selected by a user during order entry.

15 Claims, 6 Drawing Sheets

(51) Int. Cl.
*G06F 19/00* (2011.01)
*G06Q 10/10* (2012.01)
*G06Q 50/22* (2012.01)

(56) References Cited

U.S. PATENT DOCUMENTS

| | | | |
|---|---|---|---|
| 5,758,095 A | 5/1998 | Albaum et al. | |
| 5,786,816 A | 7/1998 | Macrae et al. | |
| 5,823,948 A | 10/1998 | Ross, Jr. et al. | |
| 5,826,237 A | 10/1998 | Macrae et al. | |
| 5,850,221 A | 12/1998 | Macrae et al. | |
| 5,867,799 A | 2/1999 | Lang et al. | |
| 5,946,659 A | 8/1999 | Lancelot et al. | |
| 5,995,937 A | 11/1999 | DeBusk et al. | |
| 6,018,713 A | 1/2000 | Coli et al. | |
| 6,024,699 A | 2/2000 | Surwit et al. | |
| 6,029,138 A | 2/2000 | Khorasani et al. | |
| 6,037,940 A | 3/2000 | Schroeder et al. | |
| 6,065,001 A | 5/2000 | Ohkubo et al. | |
| 6,082,776 A | 7/2000 | Feinberg | |
| 6,149,585 A | 11/2000 | Gray | |
| 6,188,988 B1 | 2/2001 | Barry et al. | |
| 6,199,115 B1 | 3/2001 | DiRienzo | |
| 6,206,829 B1 | 3/2001 | Iliff | |
| 6,230,142 B1 | 5/2001 | Benigno et al. | |
| 6,234,964 B1 | 5/2001 | Iliff | |
| 6,283,761 B1 | 9/2001 | Joao | |
| 6,289,316 B1 | 9/2001 | Aghili et al. | |
| 6,317,719 B1 | 11/2001 | Schrier et al. | |
| 6,480,837 B1 | 11/2002 | Dutta | |
| 6,873,982 B1 | 3/2005 | Bates et al. | |
| 6,886,010 B2 | 4/2005 | Kostoff | |
| 6,963,850 B1 | 11/2005 | Bezos et al. | |
| 6,983,423 B2 | 1/2006 | Dvorak et al. | |
| 7,076,436 B1 | 7/2006 | Ross et al. | |
| 7,181,438 B1 | 2/2007 | Szabo | |
| 7,225,180 B2 | 5/2007 | Donaldson et al. | |
| 7,406,436 B1 | 7/2008 | Reisman | |
| 7,447,644 B2 | 11/2008 | Brandt et al. | |
| 7,454,360 B2 | 11/2008 | Rosenfeld et al. | |
| 7,483,871 B2 | 1/2009 | Herz | |
| 7,533,353 B2 | 5/2009 | Dvorak et al. | |
| 7,742,931 B2 | 6/2010 | Miller | |
| 7,904,822 B2 * | 3/2011 | Monteleone et al. | 715/764 |
| 8,117,549 B2 * | 2/2012 | Reiner | 715/751 |
| 8,498,880 B2 * | 7/2013 | Nedblake et al. | 705/2 |
| 2002/0032583 A1 | 3/2002 | Joao | |
| 2003/0036925 A1 * | 2/2003 | Miller | 705/2 |
| 2003/0037041 A1 | 2/2003 | Hertz | |
| 2003/0115083 A1 * | 6/2003 | Masarie et al. | 705/2 |
| 2004/0128169 A1 | 7/2004 | Lusen | |
| 2004/0153341 A1 | 8/2004 | Brandt et al. | |
| 2004/0243545 A1 * | 12/2004 | Boone et al. | 707/707 |
| 2005/0004885 A1 | 1/2005 | Pandian et al. | |
| 2005/0203773 A1 * | 9/2005 | Soto et al. | 705/2 |
| 2006/0036619 A1 | 2/2006 | Fuerst et al. | |
| 2006/0143093 A1 | 6/2006 | Brandt et al. | |
| 2006/0160074 A1 | 7/2006 | Dorn et al. | |
| 2006/0248074 A1 | 11/2006 | Carmel et al. | |
| 2006/0255136 A1 | 11/2006 | Wagner et al. | |
| 2007/0250769 A1 | 10/2007 | Bass et al. | |
| 2007/0250783 A1 | 10/2007 | Wu et al. | |
| 2008/0077446 A1 | 3/2008 | Korpman et al. | |
| 2008/0312965 A1 | 12/2008 | Meshginpoosh | |
| 2009/0063189 A1 * | 3/2009 | Hupke et al. | 705/3 |
| 2009/0132598 A1 | 5/2009 | DeHaan | |
| 2010/0179852 A1 | 7/2010 | Tomizuka et al. | |

OTHER PUBLICATIONS

Sittic, et al., "Computer-based Physician Order Entry: The State of the Art", Journal of the American Medical Informatics Association, vol. 1, No. 2, Mar./Apr. 1994.

Salton and Buckley, "Term Weighting Approaches in Automatic Text Retrieval", Information Processing and Management (1988) 24:5 pp. 513-523.

\* cited by examiner

ADAPTIVELY OPTIMIZING ORDER ENTRY SYSTEM

This application is a divisional patent application of U.S. patent application Ser. No. 12/268,776 filed Nov. 11, 2008 which claims the benefit of provisional application Ser. No. 60/988,120 filed Nov. 15, 2007, by J. DeHaan.

FIELD OF THE INVENTION

This invention concerns a system for adaptively updating template medical candidate treatment order sets for use by a physician, in ordering treatment to be administered to a patient using a computerized order entry (CPOE) system, for example.

BACKGROUND OF THE INVENTION

A Clinical Information system (CIS) may use a large number of templates (such as clinical assessment forms and order sets i.e. lists of candidate treatment items for order for administration to a patient) that users can select to facilitate data entry and ordering treatment for a patient. A more advanced CIS may select the templates for the user and may also combine multiple templates into a single ad-hoc template deemed to be appropriate for a current situation. Templates used to create ad-hoc templates typically contain fewer items than templates selected by the user. As a result, the number of templates used by a more advanced CIS is significantly higher (many thousands rather than hundreds). This makes it difficult to identify which templates need to be modified and what content or template selection criteria needs to be changed to yield the highest benefit for overall use of the CIS. Anecdotal evidence and personal experience is no longer sufficient.

Known CIS systems do not compile statistics on how often template items are used, how often those items were not used and how many items were added by the users on an ad-hoc basis to complete a data entry task. System administrators and analysts use anecdotal evidence (like user complaints and change requests), personal experience or sometimes statistics collected on an ad-hoc basis to identify which templates should be changed and what changes should be made to yield a highest cost-benefit trade-off.

Changes made to templates in known systems are typically sub-optimal because incomplete and sometimes misleading information is used to determine what to change. Priorities are often based on subjective criteria (such as who complains the loudest) rather than on objective criteria that point to the highest benefits for an entire CIS user community. Also, users are apt to accept without formally complaining, larger then necessary templates, because the required data is on the template. It just takes more time the scroll up or down to find it. This lengthens data entry tasks unnecessarily because opportunities to remove unused items from templates go unnoticed.

A system according to invention principles addresses the identified deficiencies and related problems and allows templates to be compared in a consistent manner and systematically identifies what templates need to be changed and which changes yield the highest benefits.

SUMMARY OF THE INVENTION

A system continuously improves treatment ordering templates by making manual and automatic changes and deletions to the templates or the data used for the automated selection or construction of such templates based on usage statistics. A system adaptively updates template candidate order sets. A repository of information comprises multiple candidate order sets individually including multiple candidate items for order and associated corresponding related order parameters. An individual item for order is associated with multiple related order parameters. A data entry monitor monitors user selection of candidate items from a candidate order set and records candidate item usage data identifying items selected by a user for order from individual particular candidate order sets for multiple different candidate order sets. A data processor determines from the candidate item usage data at least one of, (a) data indicative of the number or proportion of candidate items of a particular candidate order set that were selected by a user during order entry and (b) data indicative of the number or proportion of candidate items of a particular candidate order set that were not selected by a user during order entry.

DETAILED DESCRIPTION OF THE INVENTION

A system continuously improves the sensitivity, specificity, precision, and accuracy of treatment order templates used by clinicians who enter orders or clinical documentation into a computerized clinical information system (CIS). A desirable order entry template (or other document template) is one that contains the items a user requires for the task at hand and no more. In that case the user does not need to modify items, add items on an ad-hoc basis, or read and scroll through items that are not needed. The system systematically improves and updates ordering templates by making manual and automatic changes to templates by adding, deleting, changing or replacing order items in a template order set, for example, or the data used for the automated selection or construction of such templates. The system adaptively updates ordering and document templates based on usage statistics. In one embodiment the usage statistics are compiled to provide a weighted Receiver Operating Characteristic (ROC), for example. The ROC enables the system to quickly identify templates and portions of a template that would benefit from updating. The data underlying the statistics identify candidate items for deleting from a template, modifications to details of an item, and the items to be added to a template. The CIS uses the statistics and underlying data to determine which items and item details to include in dynamically generating a template based on the input provided by a user preparing clinical treatment orders and documentation for a patient.

A template as used herein comprises a form or displayed arrangement of cells or data fields for presenting data items. A processor as used herein is a device for executing stored machine-readable instructions for performing tasks and may comprise any one or combination of, hardware and firmware. A processor may also comprise memory storing machine-readable instructions executable for performing tasks. A processor acts upon information by manipulating, analyzing, modifying, converting or transmitting information for use by an executable procedure or an information device, and/or by routing the information to an output device. A processor may use or comprise the capabilities of a controller or microprocessor, for example. A processor may be electrically coupled with any other processor enabling interaction and/or communication there-between. A processor comprising executable instructions may be electrically coupled by being within stored executable instruction enabling interaction and/or communication with executable instructions comprising another processor. A user interface processor or generator is a known element comprising electronic circuitry or software or a combination of both for generating display images or portions thereof. A user interface comprises one or more display images enabling user interaction with a processor or other device.

An executable application comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters. A user interface (UI), as used herein, comprises one or more display images, generated by a user interface processor and enabling user interaction with a processor or other device and associated data acquisition and processing functions.

The UI also includes an executable procedure or executable application. The executable procedure or executable application conditions the user interface processor to generate signals representing the UI display images. These signals are supplied to a display device which displays the image for viewing by the user. The executable procedure or executable application further receives signals from user input devices, such as a keyboard, mouse, light pen, touch screen or any other means allowing a user to provide data to a processor. The processor, under control of an executable procedure or executable application, manipulates the UI display images in response to signals received from the input devices. In this way, the user interacts with the display image using the input devices, enabling user interaction with the processor or other device. The functions and process steps herein may be performed automatically or wholly or partially in response to user command. An activity (including a step) performed automatically is performed in response to executable instruction or device operation without user direct initiation of the activity. An object or data object comprises a grouping of data, executable instructions or a combination of both or an executable procedure.

Workflow comprises a sequence of tasks performed by a device or worker or both. A workflow processor, as used herein, processes data to determine tasks to add to a task list, remove from a task list or modifies tasks incorporated on, or for incorporation on, a task list. A task list is a list of tasks for performance by a worker or device or a combination of both. A workflow processor may or may not employ a workflow engine. A workflow engine, as used herein, is a processor executing in response to predetermined process definitions that implement processes responsive to events and event associated data. The workflow engine implements processes in sequence and/or concurrently, responsive to event associated data to determine tasks for performance by a device and or worker and for updating task lists of a device and a worker to include determined tasks. A process definition is definable by a user and comprises a sequence of process steps including one or more, of start, wait, decision and task allocation steps for performance by a device and or worker, for example. An event is an occurrence affecting operation of a process implemented using a process definition. The workflow engine includes a process definition function that allows users to define a process that is to be followed and includes an Event Monitor, which captures events occurring in a Healthcare Information System. A processor in the workflow engine tracks which processes are running, for which patients, and what step needs to be executed next, according to a process definition and includes a procedure for notifying clinicians of a task to be performed, through their worklists (task lists) and a procedure for allocating and assigning tasks to specific users or specific teams. A document or record comprises a compilation of data in electronic form and is the equivalent of a paper document and may comprise a single, self-contained unit of information.

Figure 1:
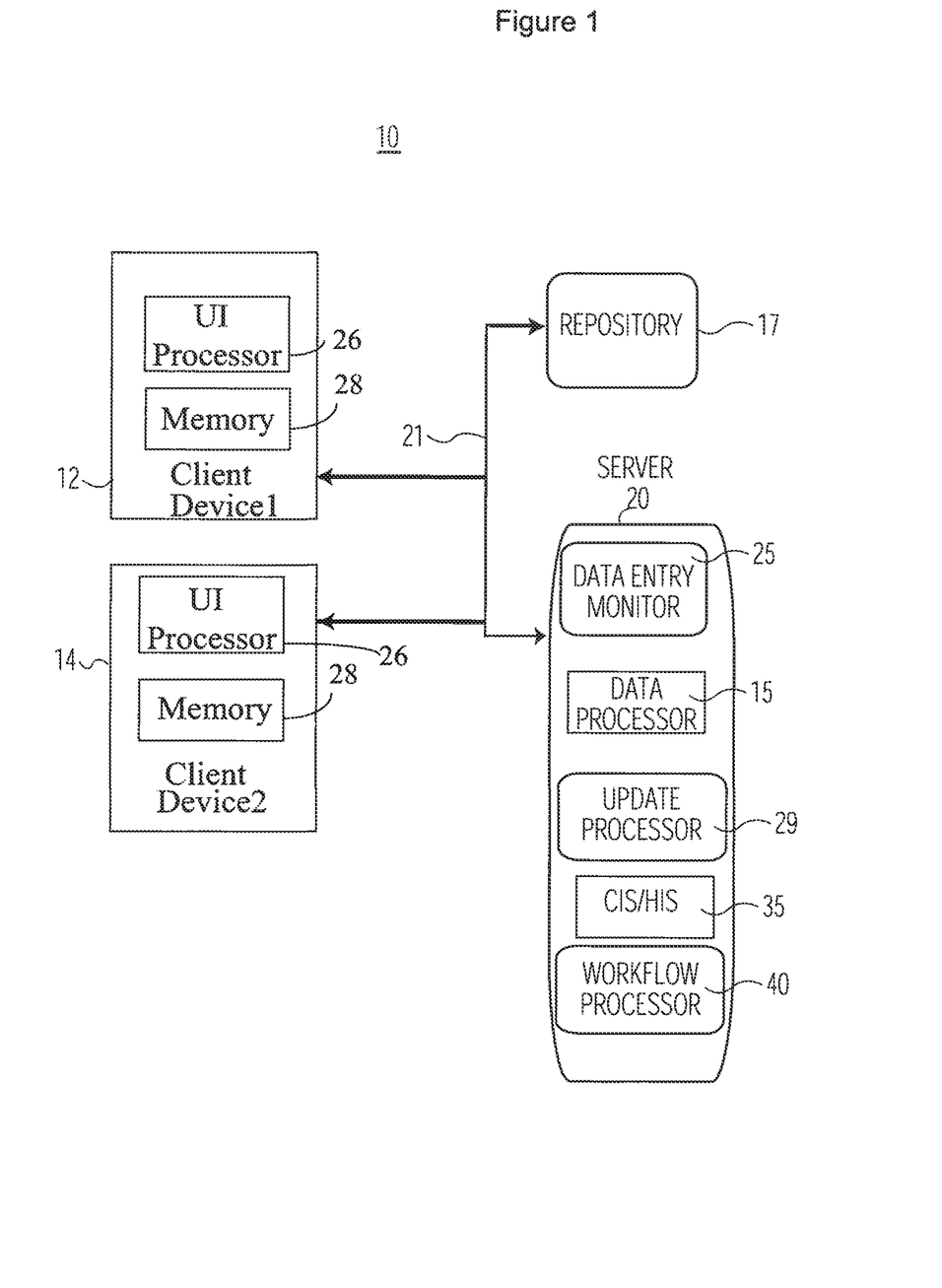
FIG. 1 shows a system for adaptively updating template candidate order sets, according to invention principles.

FIG. 1 shows system 10 for adaptively updating template candidate order sets. System 10 includes client devices (workstations) 12 and 14, repository 17 and server 20. Repository 17 (comprising one or more local or remote databases) includes information comprising multiple template candidate order sets individually including multiple candidate items for order and associated corresponding related order parameters and associates an individual item for order with multiple related order parameters. Repository 17 also includes electronic patient medical records, data representing recommended guidelines for treating different medical conditions, individual treatment order templates, medical documentation templates, treatment orders placed by physicians for patients and patient treatment plans and documentation indicating compliance with recommended treatment guidelines, for example. Server 20 includes data entry monitor 25 for monitoring user selection of candidate items from a candidate order set and recording candidate item usage data identifying items selected by a user for order from individual particular candidate order sets for multiple different candidate order sets.

Data processor 15 determines from the candidate item usage data at least one of, (a) data indicative of the number or proportion of candidate items of a particular candidate order set that were selected by a user during order entry and (b) data indicative of the number or proportion of candidate items of a particular candidate order set that were not selected by a user during order entry. Update processor 29 automatically updates a particular candidate order set by at least one of, (a) removing a candidate item, (b) adding a candidate item and (c) modifying a candidate item. Update processor 29 may also (or as an alternative) automatically generate a message for communication to a user. The message identifies candidate items that may be removed from a particular candidate order set and candidate items that may be added to a particular candidate order set. Update processor 29 may also (or as an alternative) automatically generate a (paper) report for communication to a user. Clinical information system (CIS) 35 is a Healthcare Information System (HIS) and includes a computerized order entry system supporting user ordering of treatment to be administered to a patient via one or more display images provided by user interface processor 26 on workstation 12 or 14. Clinical information system 35 presents forms to users via workstation 12 or 14 enabling a user to enter documentation for the patient indicating data identifying which tests were ordered, the medical condition of the patient and reasons for ordering medications or not ordering medications, for example. Workflow task processor 40 prompts a user (e.g., healthcare worker) with order related tasks and to complete documentation, indicating an action taken by the healthcare worker in treating the patient, and documenting compliance with the recommended guidelines.

The system 10 devices are interconnected and bidirectionally communicate via network 21 such as a LAN (Local Area Network) or other type of network. A client device (workstation) 12 or 14 includes user interface processor 26 and memory unit 28 and may comprise a personal computer, notebook, PDA, phone or other portable or fixed computerized processing device. System 10 may be used by a healthcare provider that is responsible for monitoring the health and/or welfare of people in its care. Examples of healthcare providers include, without limitation, a hospital, a nursing home, an assisted living care arrangement, a home health care arrangement, a hospice arrangement, a critical care arrangement, a health care clinic, a physical therapy clinic, a chiropractic clinic, and a dental office. Examples of the people being serviced by the healthcare provider include, without limitation, a patient, a resident, and a client.

System 10, in one embodiment, employs a Receiver Operating Characteristic (ROC) in processing data entry templates, e.g., for treatment order entry or clinical documentation entry. For an individual template, system 10 determines how often individual items in individual templates are used or selected in response to a selection command, how often individual items were not used, and which items were added to the template on an ad-hoc basis by a user. From this and other information, system 10 calculates sensitivity and new-specificity (as defined later) of an individual template. This information is plotted as a single marker on a scatter diagram, for example, which uses sensitivity and new-specificity (or 1-new-specificity) as x and y axes. System 10 plots individual template sensitivity and specificity as a marker on a scatter diagram for multiple templates.

Receiver Operating Characteristic (ROC) curves are known and used in multiple fields including medicine to determine appropriateness of diagnostic procedures and clinical guidelines, for example. However, known systems fail to automate update of templates and template selection criteria. System 10 applies objective criteria to multiple templates (including large numbers of templates) to identify candidate data entry template changes that will result in the highest cost-benefit trade-off for a CIS user population and prioritizes template maintenance. Update processor 29 automatically updates (or in one embodiment partially automatically updates), template selection criteria or template content. Data entry monitor 25 continuously monitors effect of automated template changes to ensure that they are appropriate. System Definitions.

A Prediction is an item in a template displayed by system 10.

An Actual Value is an item also included in orders or documents submitted by a user.

A True Positive is an item in a template displayed by system 10 and also included in orders or documents submitted by a user.

A False Positive is an item in a template displayed by system 10 that is not included in orders or documents submitted by a user.

A False Negative is an item that is not in a template displayed by system 10, but that is included in orders or documents submitted by a user after the user searched for it in a system catalog or entered it as free text.

A True Negative is an item that is not in a template displayed by system 10 and that is not included in orders or documents submitted by a user.

Figure 2:
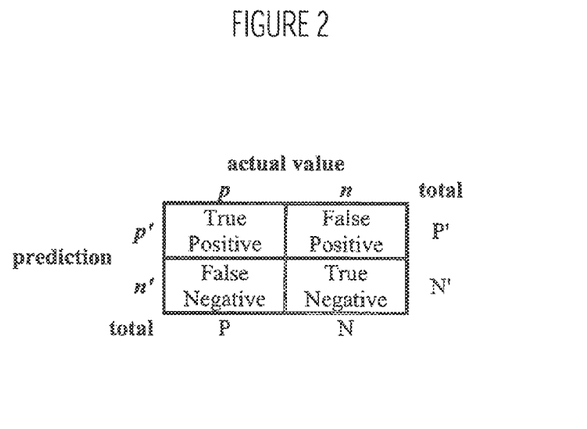
FIG. 2 illustrates interpretation of Receiver Operating Characteristic parameters.

FIG. 2 illustrates interpretation of Receiver Operating Characteristic parameters comprising Prediction items (an item in a template) and Actual Value items (a template item actually selected in Treatment orders or clinical documents submitted by a user) in quadrants corresponding to True Positive, False Positive, False Negative and True Negative.

Table of Definitions

| | |
|---|---|
| true positive (TP) | equivalent to a hit |
| true negative (TN) | equivalent to a correct rejection |
| false positive (FP) | equivalent to a false alarm, (a Type I error) |
| false negative (FN) | equivalent to a miss, (a Type II error) |
| true positive rate (TPR) | equivalent to hit rate, recall, sensitivity $TPR = TP/P = TP/(TP + FN)$ |
| false positive rate (FPR) | equivalent to a false alarm rate $FPR = FP/N = FP/(FP + TN)$ |
| accuracy (ACC) | $ACC = (TP + TN)/(P + N)$ |
| Conventional Specificity (CONVSPC) | $CONVSPC = TN/(FP + TN) = 1 - FPR$ |
| positive predictive value (PPV) | equivalent to precision $PPV = TP/(TP + FP)$ |
| negative predictive value (NPV) | $NPV = TN/(TN + FN)$ |
| false discovery rate (FDR) | $FDR = FP/(FP + TP)$ |

Figure 3:
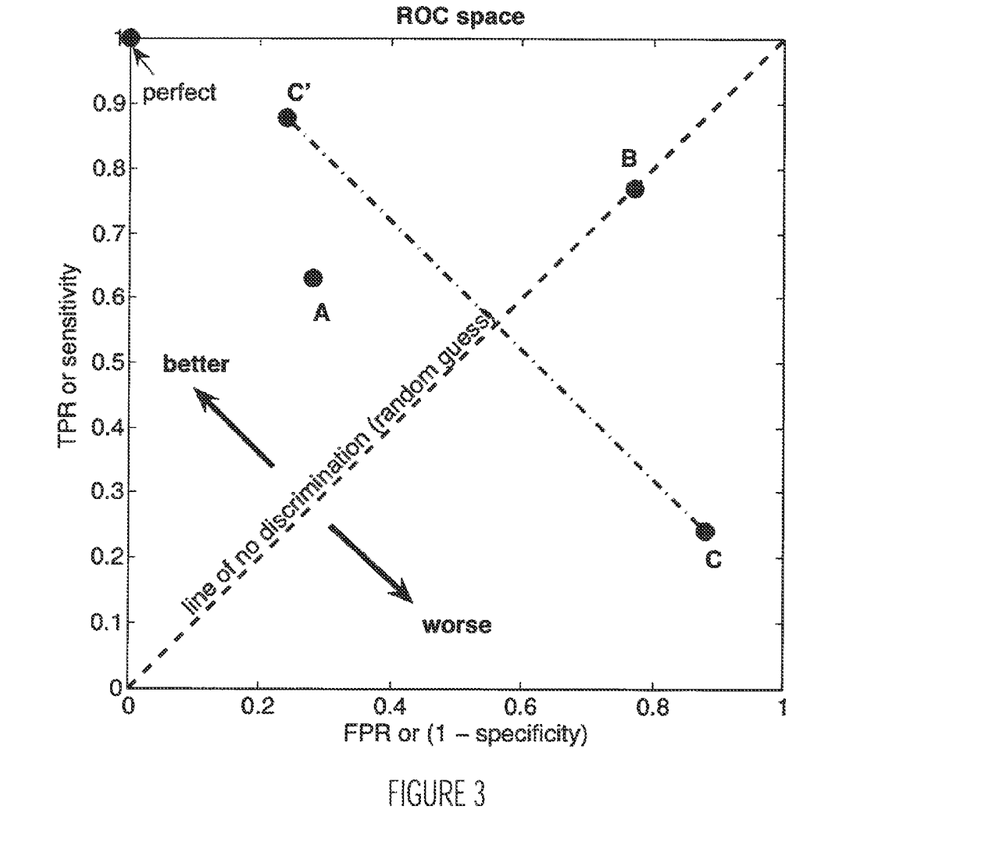
FIG. 3 shows a scatter diagram presenting generalized template order set or order item, sensitivity (or True Positive Rate—TPR) plotted against False Positive Rate (FPR or (1-specificity)) in a scatter diagram.

FIG. 3 shows general sensitivity (or True Positive Rate—TPR) plotted against False Positive Rate (FPR or (1-conventional specificity)) in a scatter diagram. In similar fashion to FIG. 2, templates scoring in the top left corner are better and in the bottom right corner are worst and most in need of automatic update by system 10. In using an ROC curve to determine appropriateness of a diagnostic test or procedure, a test is deemed to be sensitive if in a large number of cases the patient has the medical condition indicated by the test and if in a relatively small number of cases the patient has the medical condition for which he or she is being tested, even though the test indicates that the patient does not have the condition (false negative). System 10 advantageously deems a template as being analogous to a diagnostic test for the purpose of updating templates and documents. A template is deemed to be sensitive if in a large number of cases most of the services ordered for a patient or most of the items documented for a patient are obtained from the template and users on average need to add few items to a template order (or document) on an ad-hoc basis due to their absence from a template. A diagnostic test is deemed to be specific if in most cases the patient does not have the medical condition when the test indicates that the patient does not have the condition, and if in a relatively small number of cases the patient has the medical condition when the test indicates that the patient does not have that condition. Similarly, system 10 determines a template is specific if it does not contain items users do not use and the number of items in a template that are not used by users is small. However, the number of items not used by users and not in the template is more or less unlimited and therefore the conventional specificity measure (CONVSPC in the Table of Definitions) is meaningless in this context. Consequently, system 10 advantageously uses a different definition of specificity, $$\text{New-specificity}^*(SPC^*) SPC^* = 1 - FDR = 1 - (FP/(FP + TP))$$

New-specificity (SPC) is the complement of the False Discovery Rate (FDR) and measures the number of unused items on a template relative to the total number of items on the template. A small value for SPC indicates a better template that is less in need of update.

A template is very sensitive if it contains items representing all or substantially all, of the services users want to order and all or substantially all, of the items users want to document, but such a template is not very specific according to the new-specificity measure. A user needs to scroll through large numbers of items in the template to find items to select. Conversely, a template is very specific according to the new-specificity measure if it contains substantially only items that a user uses and not more, but such a template is not very sensitive because users often need to search a system catalog to find items that are not in a template or need to enter an item in free text. A good template therefore is a balance between sensitivity and new-specificity. System 10 predicts items a user wants to use in a template in a current context. In one embodiment, system 10 provides ROC curves that are a mirror image of conventional ROC curves and divide a scatter diagram into four quadrants as illustrated in FIG. 2, to facilitate determination of when and how to update a template falling into a particular quadrant.

Figure 4:
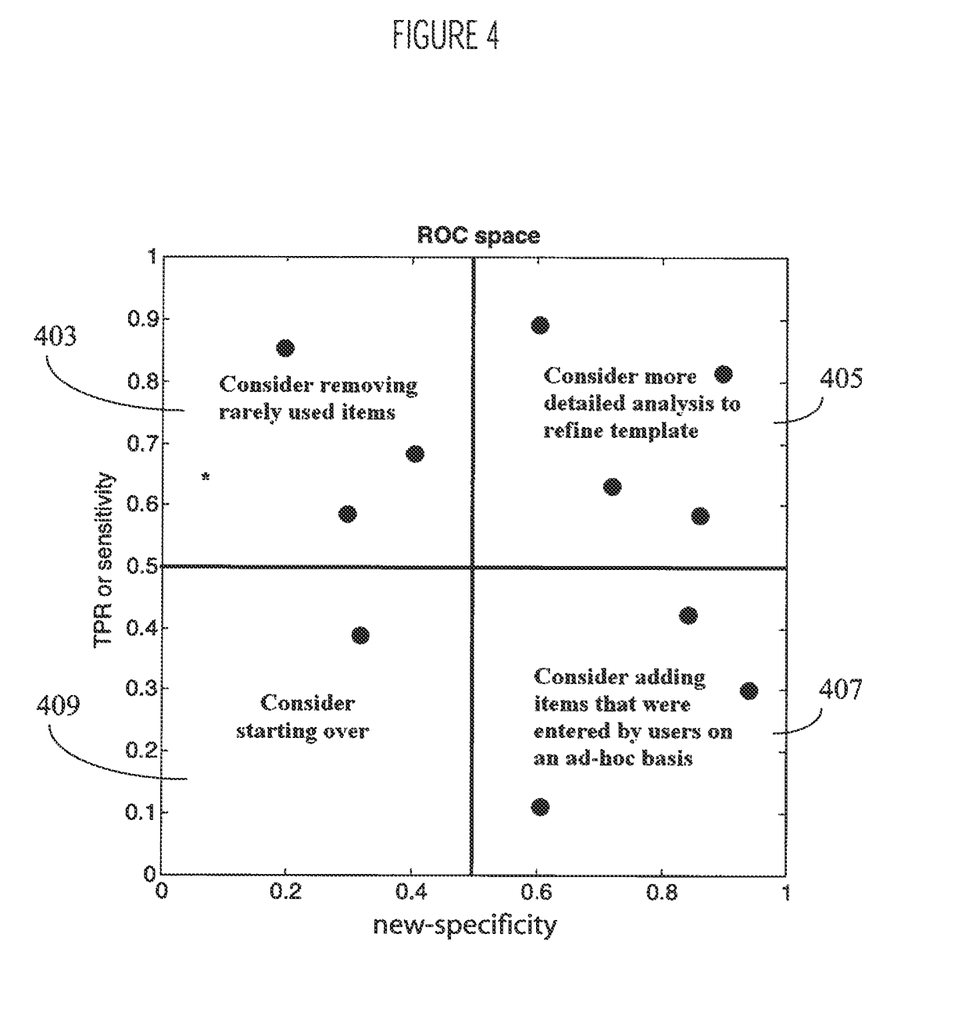
FIG. 4 illustrates a scatter diagram of treatment order template usage for determining when and how to update a template, according to invention principles.

FIG. 4 illustrates a scatter diagram of treatment order template usage divided into four quadrants for determining when and how to update a template. The scatter diagram is a plot of new-specificity on the horizontal axis against sensitivity on the vertical axis. Data processor 15 (FIG. 1) uses data indicating candidate item usage to determine at least one of, (a) data indicative of the number or proportion of candidate items of a particular candidate order set that were selected by a user during order entry and (b) data indicative of the number or proportion of candidate items of a particular candidate order set that were not selected by a user during order entry. Data processor 15 employs the determined data to provide the FIG. 4 scatter diagram. If the particular candidate order set (a template) is in quadrant 403, update processor 29 removes infrequently used candidate items from the particular candidate order set. If the particular candidate order set is in quadrant 405, data processor 15 performs a more detailed analysis of candidate item usage that is used to initiate candidate order set modification by update processor 29. If the particular candidate order set is in quadrant 407, update processor 29 adds candidate items entered by users on an ad-hoc basis to the particular candidate order set. If the particular candidate order set is in quadrant 409, data processor 15 initiates a further analysis of usage of the particular candidate order set Low template sensitivity indicates a need for a user to enter many data items into a template on an ad-hoc basis because these desired items are not available in the template. Low new-specificity indicates a need for a user to engage in extensive scrolling because the template contains a lot of unused items that are available for selection just in case the user needs them. Looking up items in the system catalog generally takes more time than scrolling through a large template. Therefore data processor 15 allocates sensitivity a different weight than new-specificity in determining whether, and how, to update available items in a template. There are multiple ways to assign weight factors, by adding a number to a value, multiplying the number by a weight factor and making a scale exponential, for example. The effect of these data processor 15 manipulations is to shift the positions of markers representing templates in a scatter diagram towards one or another quadrant. This advantageously aids a user in viewing a presented scatter diagram or aids update processor 29 in automatically evaluating scatter diagram data, to identify which templates need updating.

Figure 5:
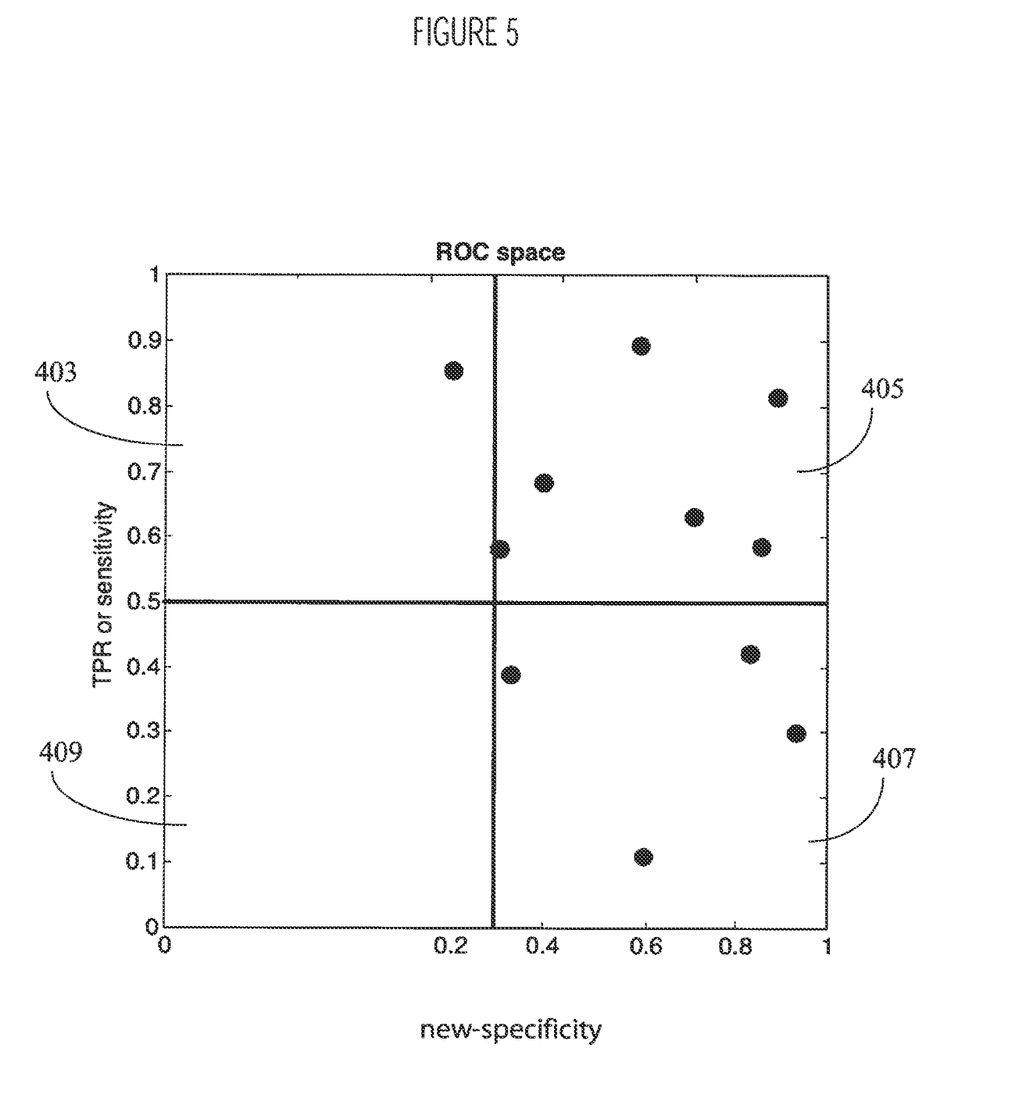
FIG. 5 illustrates a scatter diagram resulting from shift in treatment order template markers resulting from weighting sensitivity relative to new-specificity, according to invention principles.

FIG. 5 illustrates a scatter diagram resulting from shift in treatment order template representative markers resulting from weighting sensitivity relative to new-specificity. Specifically, FIG. 5 illustrates a scatter diagram showing shift in the markers of the FIG. 4 scatter diagram resulting from weighting sensitivity relative to new-specificity. Many different shifts are possible depending on the weighting method employed, however, such shifts move the positions of markers representing templates to advantageously facilitate identification of templates to be updated. As a result of the shifts, more template representative markers are moved into quadrants 405 and 407. This indicates more templates in quadrant 405 are categorized as requiring detailed analysis of candidate item usage prior to initiating candidate order set modification and more templates in quadrant 407 are categorized as requiring addition of candidate items entered by users.

Figure 6:
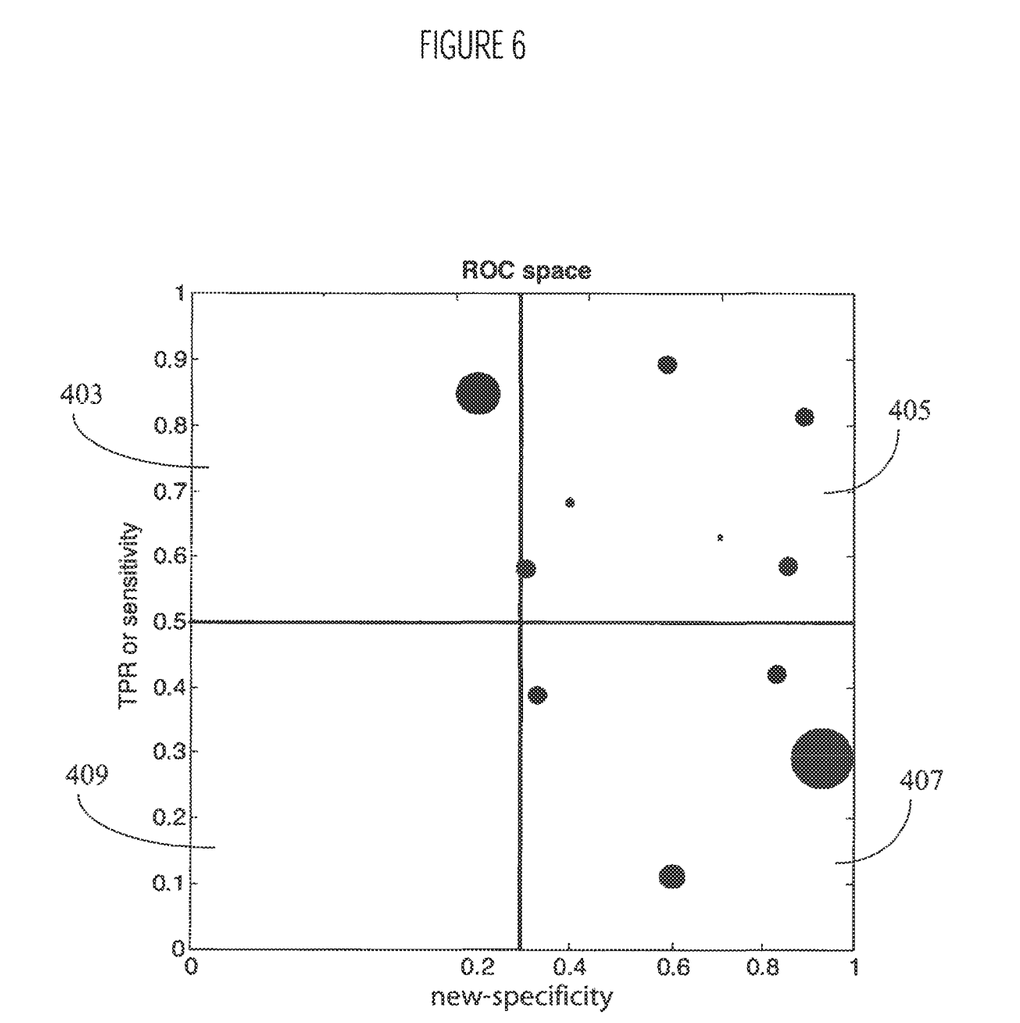
FIG. 6 illustrates a scatter diagram indicating frequency of use of treatment order templates by size of treatment order template representative markers, according to invention principles.

FIG. 6 illustrates a scatter diagram indicating frequency of use of treatment order templates by size of treatment order template representative markers. Large markers indicate high usage, therefore are allocated a high priority for template modification by data processor 15. Specifically, FIG. 6 illustrates a scatter diagram showing relative frequency of use of the FIG. 5 treatment order templates by size of treatment order template representative markers.

For each set of treatment orders or clinical documentation template items submitted by a user, data entry monitor 25 compares the content of a submitted set to the templates used by a user to construct (author) the content. The system labels the content of the submitted set (or a copy thereof) with different indicators. A first indicator indicates, a user copied an item from a template and identifies a template that contained the copied item. A second indicator indicates a user changed part of a copied item (like an order attribute such as the dose of a drug) and for an individual item identifies whether a user selected the new item content from a list of choices offered by the template, or if the user provided the item content. A third indicator indicates a user searched a system catalog for an item and selected the item from the search results. A fourth indicator indicates a user entered the content of an item without referring to data available in the system.

In response to a request, data entry monitor 25 compiles statistics from the labeled data. The compiled statistics include, the number of items selected or copied from a template with or without modification of those items, the number of template items displayed but not used, the number of items users added on an ad-hoc basis because they were not in the template. These statistics may be filtered based on one or more criteria such as (but not limited to), manually selected templates versus templates selected by system 10 at the point of use, specialty of a user, template selection criteria used by system 10 at point of use of the template (such as patient age and gender, identified patient problems, goals) and time period during which the templates were used. System 10 may exclude from analysis those template items that have been identified as mandatory due to regulations or hospital policies. In one embodiment user interface 26 displays or renders ROC curve scatter diagrams as previously described facilitating user selection of templates to be updated by update processor 29. In another embodiment, data processor 15 automatically analyzes scatter diagram data to identify templates to update and the data items to be added, deleted or modified and update processor 29 automatically updates identified templates and data items based on the analysis. Data processor 15 does this by identifying templates in particular quadrants via predetermined quadrant thresholds, for example. Data processor 15 identifies items to be automatically added, modified and removed based on statistics recorded by data entry monitor 25 and automatically adds, modifies or removes items based on template quadrant.

Alternatively, data processor 15 applies (modifiable) rules to determined sensitivity and new-specificity statistics and underlying data to determine which changes system 10 needs to make to which templates to improve overall quality and usability of treatment ordering and clinical documentation. Data processor 15 produces ROC curve scatter diagrams for use in monitoring the system ability to automatically improve and update data entry templates. In addition, besides sensitivity and new-specificity values, data processor 15 produces statistics like precision, accuracy and others previously described to produce scatter diagrams that take two variables into account. In one embodiment, system 10 compiles and filters template usage data and presents the sensitivity and new-specificity statistics in ROC diagrams, for example. However, the same template usage data collected by system 10 is also used to calculate other measures of template candidate order item quality. Examples of such other measures include, the total or average number of times treatment orders or documentation items belonging to a particular template were presented to a user in a particular time period, but that were not used for patient care and the total or average number of number of treatment orders or documentation items users had to find in the system catalog or enter as free text while the template was presented to the user. Additional determined measures comprise ratios of these other measures.

In another embodiment, system 10 collects template usage data and computes and stores summary statistics like total number of template items not used for each usage of a template and uses the summary statistics without retaining the information about which specific items where not used. Other embodiments may collect detailed template usage data, but stores the collected data separately (e.g., in a log file) from the template or separately from the treatment items ordered or documented for a particular patient while maintaining references to the template or the order or clinical documentation session.

Figure 7:
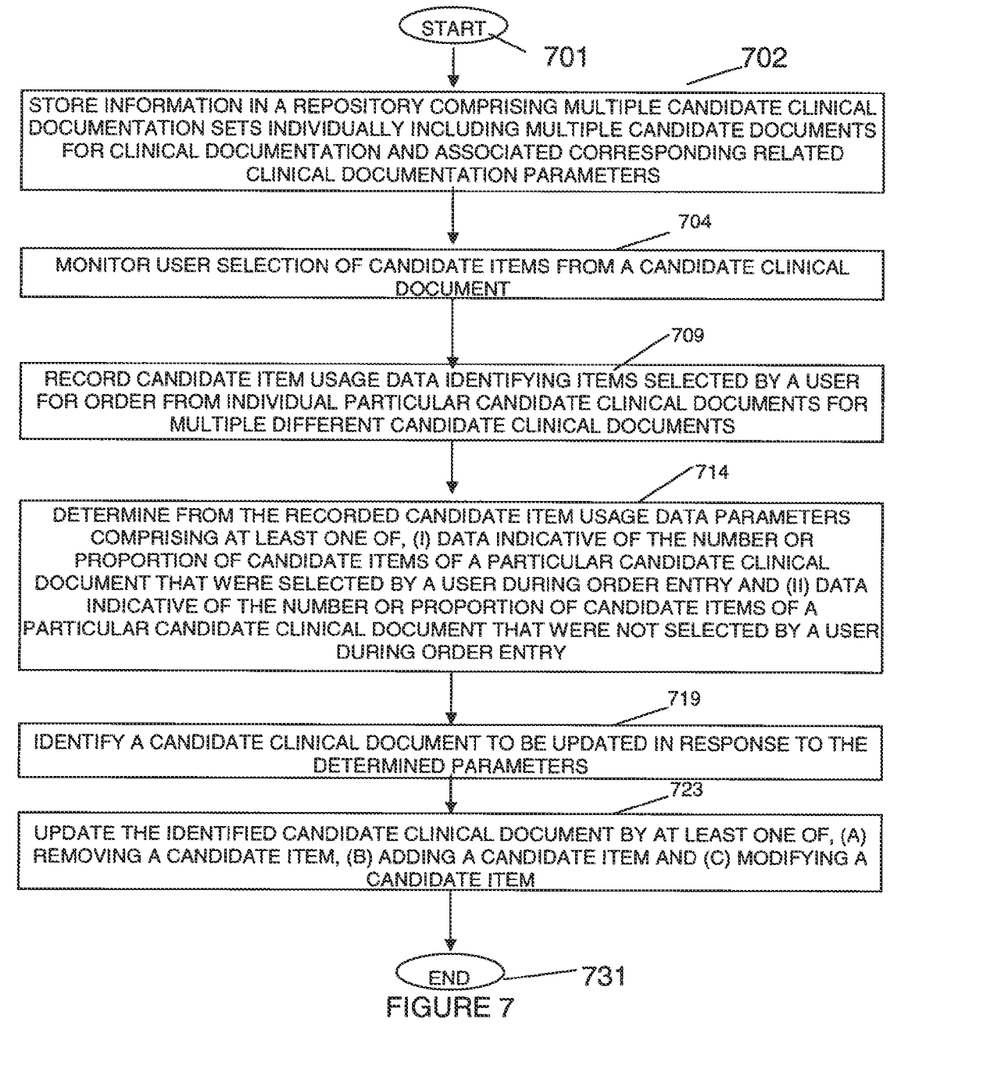
FIG. 7 shows a flowchart of a process used by a system for adaptively updating template candidate clinical documents including order sets, according to invention principles.

FIG. 7 shows a flowchart of a process used by system 10 for adaptively updating template candidate clinical documents including order sets. Further, in one embodiment a clinical document comprises a treatment order set. In step 702, following the start at step 701, data processor 15 stores information in repository 17 comprising multiple candidate clinical documentation sets (e.g. template order sets) individually including multiple candidate documents (or orders) for clinical documentation and associated corresponding related clinical documentation parameters (e.g., treatment order related parameters). An individual document for clinical documentation being associated with multiple related clinical documentation parameters. Data entry monitor 25 in step 704 monitors user selection of candidate items from a candidate clinical document (e.g., order set) and in step 709 records candidate item usage data identifying items selected by a user for use in individual particular candidate clinical documents (e.g., candidate order sets) for multiple different candidate clinical documents. Data entry monitor 25 also records document usage data identifying documents selected by a user from individual particular candidate clinical documentation sets for multiple different candidate clinical documentation sets. Data entry monitor 25 monitors orders and clinical document items entered by a user in addition to selecting candidate items from a candidate order set or candidate document template.

In step 714, data processor 15 determines from the recorded candidate item usage data parameters comprising at least one of, (i) data indicative of the number or proportion of candidate items of a particular candidate clinical document (e.g. order) that were selected by a user during data (e.g., order) entry and (ii) data indicative of the number or proportion of candidate items of a particular candidate clinical document (e.g., order set) that were not selected by a user during data (e.g., order) entry. The data indicative of the number or proportion of candidate items of a particular candidate order set that were selected by a user during order entry comprises data indicative of the number or proportion of items ordered by the user that were in a candidate order set. Data processor 15 also determines from the recorded candidate document usage data parameters comprising at least one of, (a) data indicative of the number or proportion of candidate documents of a particular candidate clinical documentation set that were selected by a user during clinical documentation entry and (b) data indicative of the number or proportion of candidate documents of a particular candidate clinical documentation set that were not selected by a user during clinical documentation entry. Data processor 15 further determines data indicative of the number or proportion of items ordered by a user that were not in a candidate order set, identifies individual candidate items of the candidate item usage data that were most frequently not selected and identifies individual candidate items of the candidate item usage data that were most frequently selected.

In step 719, data processor 15 identifies a candidate clinical document (e.g., a candidate order set) to be updated in response to the determined parameters including a weighted Receiver Operating Characteristic (ROC) derived using the determined parameters. Data processor 15 identifies multiple candidate clinical documents to be updated in response to the determined parameters and prioritizes candidate clinical documents to be updated based on frequency of use of use of the candidate clinical documents. Data processor 15 further identifies an individual candidate item of a particular candidate clinical document that was not selected by a user during data entry based on a frequency of non-selection exceeding a predetermined threshold non-selection frequency or for a proportion of times exceeding a predetermined proportion. In one embodiment, user interface 26 presents in a display image a diagram (e.g., a Receiver Operating Characteristic) indicating at least one of, (a) candidate items that may be removed from a particular candidate order set and (b) candidate items that may be added to a particular candidate order set. In step 723, update processor 29 automatically (or in one embodiment in response to user command) updates the identified candidate clinical document (e.g., order set) by at least one of, (a) removing a candidate item, (b) adding a candidate item and (c) modifying a candidate item. Update processor 29 also automatically generates a message or report for communication to a user identifying at least one of, (a) candidate items that may be removed from a particular candidate order set and (b) candidate items that may be added to a particular candidate order set. The process of FIG. 7 terminates at step 731.

The systems and processes of FIGS. 1-7 are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. Further, the processes and applications may, in alternative embodiments, be located on one or more (e.g., distributed) processing devices. Any of the functions and steps provided in FIGS. 1-7 may be implemented in hardware, software or a combination of both.

What is claimed is:

1. A system for use in adaptively updating template candidate order sets, comprising:
    a repository of information comprising a plurality of candidate order sets individually including a plurality of candidate items for order and associated corresponding related order parameters, an individual item for order being associated with a plurality of related order parameters;
    a data entry monitor for monitoring user selection of candidate items from a candidate order set acquired from said repository and recording candidate item usage data identifying items selected by a user for order from individual particular candidate order sets for a plurality of different candidate order sets; and
    a data processor device for determining from the recorded candidate item usage data parameters comprising at least one of, (a) data indicative of the number or proportion of candidate items of a particular candidate order set that were selected by a user during order entry and (b) data indicative of the number or proportion of candidate items of a particular candidate order set that were not selected by a user during order entry, said data processor device automatically identifies, based on the determined parameters, a candidate order set from the plurality of candidate order sets to be updated.

2. A system according to claim 1, wherein
said data entry monitor monitors orders entered by a user in addition to selecting candidate items from a candidate order set.

3. A system according to claim 1, wherein
said data processor device determines data indicative of the number or proportion of items ordered by a user that were not in a candidate order set.

4. A system according to claim 1, wherein
said data indicative of the number or proportion of candidate items of a particular candidate order set that were selected by a user during order entry comprises data indicative of the number or proportion of items ordered by the user that were in a candidate order set.

5. A system according to claim 1, wherein
said data processor device identifies individual candidate items of said candidate item usage data that were most frequently not selected.

6. A system according to claim 1, wherein
said data processor device identifies individual candidate items of said candidate item usage data that were most frequently selected.

7. A system according to claim 1, including
an update processor for automatically generating a message for communication to a user identifying at least one of, (a) candidate items that may be removed from a particular candidate order set and (b) candidate items that may be added to a particular candidate order set.

8. A system according to claim 1, including
a user interface for presenting in a display image a diagram indicating at least one of, (a) candidate items that may be removed from a particular candidate order set and (b) candidate items that may be added to a particular candidate order set.

9. A system according to claim 8, wherein said diagram is an ROC chart.

10. A system according to claim 1, including
an update processor for automatically updating a particular candidate order set by at least one of, (a) removing a candidate item, (b) adding a candidate item and (c) modifying a candidate item.

11. A system according to claim 1,
including
an update processor for updating an the identified candidate order set by at least one of, (a) removing a candidate item, (b) adding a candidate item and (c) modifying a candidate item.

12. A system according to claim 1, wherein
said data processor device identifies the candidate order set is to be updated in response to a weighted Receiver Operating Characteristic (ROC) derived using the determined parameters.

13. A system according to claim 11, wherein
said item comprises candidate treatment order parameters and candidate order parameter values.

14. A system according to claim 1, wherein
said data processor device identifies the candidate order set to be updated in response to statistics derived using the determined parameters.

15. A system according to claim 1, wherein said statistics comprise sensitivity and new-specificity statistics.

* * * * *